United States Patent [19]

Drake et al.

[11] Patent Number: 4,940,831
[45] Date of Patent: Jul. 10, 1990

[54] PURIFICATION OF CIS-OLEFINS

[75] Inventors: Charles A. Drake, Nowata; Jim D. Byers; Steven D. Bridges; both of Bartlesville, all of Okla.

[73] Assignee: Phillips Petroleum Company, Bartlesville, Okla.

[21] Appl. No.: 312,103

[22] Filed: Feb. 15, 1989

[51] Int. Cl.$^5$ ............................................... C07C 7/17
[52] U.S. Cl. ..................................... 585/836; 585/866; 585/868
[58] Field of Search ............... 585/833, 836, 856, 866, 585/868, 324

[56] References Cited

U.S. PATENT DOCUMENTS

| | | | |
|---|---|---|---|
| 3,444,261 | 5/1969 | Caprioli et al. | 585/809 |
| 3,492,343 | 1/1970 | Garner et al. | 585/811 X |
| 4,364,931 | 6/1982 | Szántay et al. | 424/84 |
| 4,609,498 | 9/1986 | Banasiak et al. | 260/410.9 R |
| 4,673,672 | 6/1987 | Houlihan et al. | 514/95 |
| 4,740,627 | 4/1988 | Byers et al. | 568/469.9 |
| 4,749,818 | 6/1988 | Byers et al. | 585/324 |

OTHER PUBLICATIONS

"Chemistry and Biochemistry of Plant Pigments", Goodwin, Academic Press, New York, 1965, p. 496.
"Comprehensive Organic Chemistry", Pergamon Press, New York, vol. 3, pp. 320–322.
"Sulfinic Acid Catalyzed Isomerization of Olefins", J. Org. Chem. 41: p. 791 (1976).
"The Reaction Between Sulfochlorides and Organomagnesium Halides", Gilman et al, pp. 3501–3508, Nov. 1929.
"The Constitution of Some Bacterial Casotenoids and their Bearing on Biosynthetic Problems", Jensen, 1962, p. 106.

*Primary Examiner*—Glenn Caldarola
*Attorney, Agent, or Firm*—Hal Brent Woodrow

[57] ABSTRACT

A method for purifying a cis-olefin formed by alkylating a sulfonate ester comprising mixing the reaction formed by alkylating a sulfonate ester with an acid solution, separating said acid solution, and mixing the resultant purification product with a $C_1$–$C_4$ alcohol and optionally a base followed by separation and distillation, or passing said reaction mixture through a silica gel and collecting the cis-olefin fraction.

22 Claims, No Drawings

PURIFICATION OF CIS-OLEFINS

FIELD OF THE INVENTION

This invention relates generally to the purification of cis-olefins.

BACKGROUND OF THE INVENTION

Cis-olefins are an important source of pharmacological and biological compounds such as pheromones. Unfortunately, the synthesis of cis-olefins is a very difficult and expensive process because of the tendency of the reaction products to isomerize into inactive or inhibitory trans-isomers. An example of a simple cis-olefin which has proven difficult to produce economically is cis-9-tricosene, a housefly pheromone.

Many of the more classical syntheses require the use of alkynes or Wittig reagents to obtain the desired cis-stereochemistry. Although these reagents produce cis-olefins in high purity, their use in large scale production of pure cis-olefins is prohibitively expensive. Many cis-olefins, however, could be economically produced in high yields via a synthesis process which uses sulfonate esters, if a method could be developed to avoid isomerization from cis- to trans-isomers during the purification of the cis-olefin product. For instance, we have discovered that cis-9-tricosene (and many other cis-olefins) can be synthesized by a simple three step process beginning with readily available cis-alcohols. The first step of this process is to deprotonate the cis-olefinic alcohol to form a lithium or sodium alkoxide salt followed by reacting the olefinic alkoxide salt to form a sulfonate ester, then alkylating the sulfonate ester with an appropriate alkylmagnesium compound and a cuprous salt. After alkylation it is usually desirable to recover the cis-olefin in a highly purified form. Most schemes for purification of the cis-olefin rely on a distillation process. Unfortunately the cis-olefin is substantially converted to a trans-olefin during distillation from the alkylating reaction mixture containing the sulfonate ester.

It would also be advantageous if a process for the purification of cis-olefins formed by alkylating a sulfonate ester could be developed which is economical, simple, and easy to scale-up.

It is an object of this invention to provide an economical process for the purification of cis-olefins produced by alkylating a sulfonate ester.

It is also an object of this invention to provide a simple, easy to scale-up process for the purification of cis-olefins formed by alkylating a sulfonate ester.

It is a further object of this invention to provide a process for the purification of cis-9-tricosene, which is produced by alkylating a sulfonate ester.

Other aspects, objects, and several advantages of this invention will be apparent from the specification, including the examples and accompanying claims.

SUMMARY OF THE INVENTION

In accordance with the present invention, we have discovered a process for the purification of a cis-olefin formed by alkylating a sulfonate ester, wherein said cis-olefin is purified from a reaction mixture formed by the alkylation of said sulfonate ester, which process comprises (a) mixing said reaction mixture with an acid solution to form a first purification mixture, (b) separating said acid solution from said first purification mixture to form a first purification product, (c) mixing said first purification product with a $C_1$-$C_4$ alcohol to form a second purification mixture, (d) separating said $C_1$-$C_4$ alcohol from said second purification mixture to form a second purification product, and (e) distilling said second purification product to yield a third purification product containing said cis-olefin.

In accordance with another embodiment of the present invention, we have also discovered a process for the purification of a cis-olefin formed by alkylating a sulfonate ester wherein said cis-olefin is purified from a reaction mixture formed by the alkylation of said sulfonate ester, which process comprises (a) passing said reaction mixture through a suitable chromatographic gel packed in an organic solvent and (b) recovering the organic fraction containing said cis-olefin.

DETAILED DESCRIPTION

In accordance with one embodiment of this invention a process is provided for the purification of a cis-olefin formed by alkylating a sulfonate ester, wherein said cis-olefin is purified from a reaction mixture formed by the alkylation of said sulfonate ester, which process comprises (a) mixing said reaction mixture with an acid solution to form a first purification mixture, (b) separating said acid solution from said first purification mixture to form a first purification product, (c) mixing said first purification product with a $C_1$-$C_4$ alcohol to form a second purification mixture, (d) separating said $C_1$-$C_4$ alcohol from said second purification mixture to form a second purification product, and (e) distilling said second purification product to yield a third purification product containing said cis-olefin.

One suitable method of forming a cis-olefin utilizing a sulfonate ester synthesis consists of (a) the deprotonation of a cis-olefinic alcohol to form a lithium or sodium salt followed by (b) the formation of a sulfonate ester and (c) the alkylation of the sulfonate ester with an alkylmagnesium compound and a cuprous salt.

To produce a cis-olefin, one need only begin with a cis-olefinic alcohol having a hydroxyl-group at the desired site or sites of alkylation and choose an appropriate alkylmagnesium compound having the desired alkyl group.

Appropriate cis-olefinic alcohols for use in the three step synthesis set forth above are non-conjugated, non-cumulated, non-enolic (without a double bond adjacent to a hydroxyl group) cis-olefinic alcohols. The cis-olefinic alcohols can also contain more than one double bond. A cis-olefinic alcohol with more than one double bond can be employed with a double bond allylic to the hydroxyl group if the allylic double bond position is inconsequential in the final cis-olefin, because said allylic double bond may shift position. Although cis-olefinic allylic alcohols may be suitable for this process, they are not recommended because of the tendency for allylic bonds to shift with the resultant isomerization to trans-olefinic alcohols. The cis-olefinic alcohols can also include glycols and polyols, however, each hydroxyl may serve as a site of alkylation.

The first step in this three step synthesis of a cis-olefin is a deprotonation reaction of a cis-olefinic alcohol with a source of an alkali metal ion selected from the group consisting of lithium and sodium ions. The first reaction product comprises an alkoxide which can be formed utilizing reagents and techniques well known to those of skill in the art. Suitable sources of alkali metal ions include, but are not limited to, alkali metal ion sources selected from the group consisting of sodium metal, lithium metal, alkyllithium, alkylsodium, aryllithium, and arylsodium. A preferred source of alkali metal ions is an alkyllithium compound selected from the group consisting of phenyllithium, butyllithium, and methyllithium. It is preferred that the temperature at which deprotonation is performed should be maintained in the range from about −70° C. to about 50° C., more preferably from about −10° C. to about 50° C. The ratio of cis-olefinic alcohol hydroxyl groups to the alkali metal ions may range from about 1:0.25 to about 1:1.5. Preferably, this ratio will range from about 1:1 to about 1:1.1. Time is not a critical factor for reacting the cis-olefinic alcohol to form a lithium or sodium alkoxide, and may vary depending upon the temperature and concentration of reactants. Generally the reaction should be allowed to reach substantial completion before the next step is begun. However, the reaction will go to completion almost as quickly as the source of alkali metal ions is mixed with the cis-olefinic alcohol.

The second step in this three step synthesis of a cis-olefin is the reaction of the first reaction product, comprising an alkoxide, with a sulfonyl halide compound to form a sulfonate ester. Sulfonyl halide compounds suitable for this three step synthesis process can be selected from the group consisting of alkylsulfonyl halides and arylsulfonyl halides wherein the sulfonyl halide will not interfere with the alkylation in the third step. For the purpose of this specification and the accompanying claims, alkylsulfonyl halides shall also include triflates, including but not limited to, trifluoromethanesulfonyl halides. Preferred sulfonyl halide compounds include, but are not limited to, those selected from the group consisting of p-toluenesulfonyl halides, p-and o-toluenesulfonyl halides, trifluromethanesulfonyl halides, methanesulfonyl halides, and benzenesulfonyl halides. The halides which can be used in sulfonyl halide compounds are selected from the group consisting of chloride and bromide. The most preferred sulfonyl halide compounds are p-toluenesulfonyl chloride and benzenesulfonyl chloride.

The reaction of the first reaction product with the sulfonyl halide compound to form the sulfonate ester, can take place under a wide variety of reaction conditions. Generally the reaction temperature will be in the range of about 0° C. to about 70° C. Preferably the reaction temperature is in the range of from about 30° C. to about 60° C. In this step of the three step synthesis of a cis-olefin, pressure is generally not critical, but will generally be in the range of from about 0 psig to about 2,000 psig. Preferably the pressure is in the range of from about 1 psig to about 25 psig.

The time of reaction for reacting a sulfonyl halide compound with a first reaction product to form a sulfonate ester will depend upon the desired degree of conversion, the reaction temperature, and concentration of sulfonyl halide and alkoxide, but will generally be that time period needed for the reaction to reach substantial completion before the next step is begun, which time period has been found to be about 1 hour. Preferably the reaction time is in the range of from about 1 hour to about 24 hours.

The third step in the three step synthesis of a cis-olefin is the reaction of the second reaction product with an alkylmagnesium compound and a cuprous salt to form a third reaction product comprising a cis-olefin. The alkylmagnesium compound may be selected from the group consisting of dialkylmagnesium and alkylmagnesium halide wherein the halide of said alkylmagnesium halide is selected from the group consisting of iodide, bromide, and chloride. Preferred for the three step synthesis of cis-olefins are alkylmagnesium halides selected from the group consisting of alkylmagnesium bromide and alkylmagnesium chloride. The alkylmagnesium compounds suitable for the practice of this invention can be synthesized by those skilled in the art using any appropriate synthesis technique.

The alkylmagnesium compound used must be selected to result in the appropriate alkyl group being transferred to the sulfonate ester. For example, if cis-oleyl alcohol were to be reacted by the present invention to cis-9-tricosene, an n-pentylmagnesium halide would be employed as the alkylmagnesium halide to alkylate the sulfonate ester of oleyl alcohol. The preferred alkylmagnesium halide for the alkylation of oleyl alcohol to cis-9-tricosene is n-pentylmagnesium chloride.

A wide variety of alkylation catalysts are capable of promoting the alkylation of the sulfonate ester with the alkylmagnesium compound. The present invention is not limited to the use of a specific alkylation catalyst. Any alkylation catalyst which will promote the alkylation of the sulfonate ester with an alkylmagnesium compound so as to produce a cis-olefin can be used. Suitable alkylation catalysts include, but are not limited to: cuprous salts selected from the group consisting of cuprous bromide, cuprous chloride, cuprous iodide, and dilithium cuprous tetrachloride. The preferred cuprous salt is cuprous bromide.

The alkylation catalyst can be employed in any suitable amount which will facilitate the alkylation of the sulfonate ester with the alkylmagnesium compound so as to produce a cis-olefin. Generally the ratio of the moles of sulfonate ester to the moles of alkylation catalyst is in the range of from about 1:1 to about 1:0.005. Preferably the ratio is in the range of from about 1:0.01 to about 1:0.05.

Although the second reaction product, said sulfonate ester and the alkylmagnesium compound, can be reacted together in about any ratio of sulfonate ester to alkylmagnesium compound, the ratio will generally be in the range of from about 10:1 to about 1:10, and preferably the ratio is in the range of from about 1:1 to about 1:2.

The alkylation of sulfonate ester with alkylmagnesium halide and cuprous salt alkylating catalyst can take place under a variety of reaction conditions. Generally the temperature of the alkylation will be in the range of from about −70° C. to about 10° C. Preferably the temperature is in the range of from about −30° C. to about 10° C., and most preferably in the range of from about −10° C. to about 5° C. In this alkylation step, pressure is not critical, but will generally be in the range of from about 0 psig to about 2,000 psig. Preferably the pressure is in the range of from about 0.1 psig to about 250 psig, and most preferably in the range of from about 1 psig to about 25 psig.

The time of the alkylation of sulfonate ester with alkylmagnesium compound will depend upon the desired degree of conversion, the reaction temperature, ratio of sulfonate ester to alkylmagnesium compound, and the alkylation catalyst utilized, but will generally depend on the speed at which the three reaction components of this step can be mixed while still keeping the reaction mixture within the recommended temperature ranges. Preferably the time is in the range of from about 1 minute to about 360 minutes, most preferably in the range of from about 5 minutes to about 120 minutes.

The preceeding three step processes will take place in a wide variety of organic solvents. Generally any organic solvent in which the reactants are soluble will be suitable. Preferably ethers such as tetrahydrofuran and diethyl ether are used as solvents. Currently preferred are organic solvents which include, but are not limited to, organic solvents selected from the group consisting of diethyl ether, methylpropyl ether, ethylpropyl ether, 2-methoxyethyl ether, and tetrahydrofuran.

The three step synthesis of cis-olefins may also be performed sequentially in one vessel. Those skilled in the art will recognize that the reactants should be utilized in ratios at each step which will be close to the stoichiometric ratios, thereby avoiding the possibility of side reactions which could interfere with the succeeding step in the process of the present invention. The process of this invention should be practiced in the substantial absence of $O_2$, $CO_2$, and $H_2O$ to avoid inactivation of the alkylmagnesium compound of the third step. The third reaction product will be predominately a cis-olefin. Those skilled in the art will recognize that other synthesis processes could be used to produce cis-olefins utilizing sulfonate esters.

To recover the desired cis-olefin synthesized utilizing a sulfonate ester it is necessary to contact the reaction mixture resulting from the alkylation of said sulfonate ester to form said cis-olefin with an acid solution, then a short chain alcohol solution and optionally a base solution.

The acid solution should consist of an aqueous acid of about 1 molar to 6 molar selected from the group consisting of hydrochloric acid, sulfuric acid, phosphoric acid, and acetic acid. The volumetric ratio of acid solution to be mixed with the reaction mixture should be from about 0.01:1 to about 100:1. Preferably the volumetric ratio of acid solution to the reaction mixture will be in the range of from about 0.5:1 to about 2:1.

The acid solution should be mixed with the reaction mixture containing the cis-olefin synthesized utilizing a sulfonate ester in a manner which facilitates thorough mixing of the acid solution and the reaction mixture. In most syntheses of cis-olefins this will require the mixing of the aqueous acid and an organic phase containing the reaction mixture. Mixing may be effectuated by mechanical agitation, stirring, or any other suitable means known to those skilled in the art.

The time in which the acid solution is in contact with the reaction mixture need only be sufficient to allow for thorough mixing of the aforesaid acid solution and reaction mixture.

The temperature at which the mixing of the acid solution and the reaction mixture should range of from about 0° C. to about 40° C. and preferably will range of from about 0° C. to about 30° C.

After the acid solution and reaction mixture have been mixed to form a first purification mixture, the purification mixture will separate into two phases. One phase will be an aqueous phase containing the acid and other soluble contaminates. The second phase will be an organic phase containing the cis-olefin. These two phases may be separated by conventional techniques known to those skilled in the art to form a first purification product. One suitable separation technique would be to decant the aqueous phase. The first purification product is then mixed with a $C_1$-$C_4$ alcohol. The amount of $C_1$-$C_4$ alcohol mixed with the first purification product should range from a volumetric ratio of from about 0.01:1 to about 100:1 preferably of from about 0.5:1 to about 2:1.

The $C_1$-$C_4$ alcohol should be contacted with the purification product containing the cis-olefin synthesized utilizing a sulfonate ester in a manner which facilitates thorough mixing of the $C_1$-$C_4$ alcohol with the aforesaid first purification product. In most syntheses of cis-olefins this will require the mixing of a $C_1$-$C_4$ alcohol with an organic phase containing the purification product. Mixing may be effectuated by mechanical agitation, stirring, or any other suitable means known to those skilled in the art.

The time in which the $C_1$-$C_4$ alcohol is mixed with the purification product need only be sufficient to allow thorough mixing of the aforesaid $C_1$-$C_4$ alcohol and purification product. The temperature at which the mixing of the $C_1$-$C_4$ alcohol and the purification product is conducted should range of from about 0° C. to about 40° C. and preferably of from about 0° C. to about 30° C.

After the $C_1$-$C_4$ alcohol and the purification product have been mixed, another purification mixture will be formed. This purification mixture will also separate to form two phases. One phase will be the methanol solution and other soluble contaminates. The second phase will be an organic phase containing the cis-olefin. The two phases may be separated by conventional techniques known to those skilled in the art to form a second purification product. Again, one suitable separation technique would be to decant the aqueous phase from the second purification mixture.

Optionally, a base may be added to the $C_1$-$C_4$ alcohol or provided as a separate aqueous solution before or after the $C_1$-$C_4$ alcohol is mixed with the first purification product. The base may consist of an base selected from the group consisting of potassium hydroxide and sodium hydroxide. The preferred base is potassium hydroxide. The concentration of the base may range from about 0.5 molar to about 4 molar with a preferred range of from about 1 molar to about 2 molar.

The quantity of base in solution, mixed with the purification product or purification mixture should range from a volumetric ratio of about 0.1:1 to about 10:1 with a preferred range of from about 0.5:1 to about 2:1.

The base in solution should be mixed with the purification product or purification mixture containing the cis-olefin in a manner which facilitates thorough mixing of the base in solution with the aforesaid purification product. Mixing may be effectuated by mechanical agitation, stirring, or any other suitable means known to those skilled in the art.

The time for which the base in solution is mixed or in contact with a purification product or purification mixture need only be sufficient to allow thorough mixing with the purification product or mixture. The temperature at which the purification product and the base in solution should be mixed should range from about 0° C. to about 40° C. and preferably will range from about 0° C. to about 30° C.

After the purification product and the base in solution are mixed, the mixture will separate into two phases. One phase will contain the base in solution and other soluble contaminates. The second phase will be an organic phase containing the cis-olefin. These two phases should be separated by conventional techniques known to those skilled in the art. One suitable separation technique would be to decant the phase containing the base in solution and other soluble contaminates.

The final purification product may be further purified by distillation. Distillation may be accomplished by conventional techniques known to those skilled in the art. Currently, preferred for the practice of this invention is distillation under reduced pressure, approximately one-tenth of a millimeter of mercury, wherein the distillation head temperature ranges from about 160° C. to about 175° C. Preferably the distillation will be performed using a column packed with an inert packing material including, but not limited to, stainless steel and the distillation head temperature will be maintained in the range of from about 165° C. to about 170° C.

In another embodiment of the present invention, another process is provided for the purification of a cis-olefin formed by alkylating a sulfonate ester wherein the cis-olefin is purified from the reaction mixture formed by the alkylation of said sulfonate ester which comprises passing said reaction mixture through a suitable silica gel packed in a nonpolar organic solvent and recovering the cis-olefin from the fraction generated therefrom. The silica gel used may be any chromotographic grade silica gel. Currently preferred are 70–230 mesh silica gels such as Kiesel gel 60 TM. The gel should be packed in a nonpolar organic solvent such as nonpolar organic solvents selected from the group consisting of hexane, pentane, and petroleum ethers. Column sizing will depend on the amount of material desired to be processed and the degree of separation desired as may be determined by one skilled in the art. Generally the amount of reaction mixture to be loaded will range from about 3 to about 4 times the weight of the silica gel.

The temperature at which the column of silica gel should be used may generally range from 0° C. to 40° C., wherein the temperature is selected below the boiling point of the nonpolar organic solvent used. The pressure at which the separation is performed is not believed to be critical to the present invention.

Additionally, the gel used in the present invention may be reused by washing contaminated gels with suitable polar solvents including, but not limited to, ethyl acetate.

The fraction to be saved containing the cis-olefin may be determined by monitoring the fraction yielded by methods including, but not limited to, GC, HPLC, or paper chromotography.

The following non-limiting examples are provided to further illustrate the practice of the present invention.

EXAMPLES

To separate and identify cis-9-tricosene, trans-9-tricosene, and tricosane, a mixture of these pure samples was injected into an HP 5880A gas chromatograph (GC). The column was a Smetic column (200 microns×25 meters) purchased from Lee Scientific, Salt Lake City, Utah. The film thickness of the column was 0.15 microns. The GC was programmed from 80° C. to 160° C. at 4° C. per minute ramping rate. The retention time for cis-9-tricosene, trans-9-tricosene, and tricosane was 16.89, 17.31, and 17.66 minutes, respectively.

EXAMPLE I

Synthesis of cis-9-tricosene

A 12 l flask equipped with a reflux condenser, Firestone valve, mechanical stirrer, and addition funnel was flushed with $N_2$. 500 g of oleyl alcohol and 1500 ml of tetrahydrofuran were added to the flask and the reaction mixture was cooled to 0° C. 1330 ml of n-butyllithium (1.6M in hexane) was added dropwise while maintaining the temperature below 5° C. The addition of butyllithium was completed in approximately 45 min. 420.6 g of p-toluenesulfonyl chloride was then added and the temperature was increased to 35°–40° C. using a heating mantle. The temperature was held at 40° C. for 3 hr. The reaction mixture was then cooled to 0° C. using a dry ice/isopropanol bath. 10 g of cuprous bromide was added followed by the dropwise addition of 1120 ml of n-pentylmagnesium bromide (2.5M in diethyl ether). This addition was completed in 48 min and the temperature was maintained near 0° C. during this time. The reaction mixture was stirred for 1 hr following the addition of n-pentylmagnesium bromide, then warmed to room temperature and held overnight under $N_2$.

EXAMPLE II

Purification of cis-9-tricosene

Crude tricosene made by the process described in Example I was treated two different ways and distilled under vacuum in order to determine whether isomerization had occurred. The first treatment involved washing with equal volumes of water, and then drying over $MgSO_4$ prior to distillation. This resulted in 30.7% cis and 43.4% trans. In the second treatment, 6.5 l of 4M HCl was added followed by phase separation. The organic phase was then washed with 3 l of saturated sodium bicarbonate solution prior to distillation. This treatment resulted in 39.0% cis and 35.2% trans determined by GC as described above.

EXAMPLE III

Purification of cis-9-tricosene Using Silica Gel

Crude tricosene made by the process described from Example I was immediately chromatographed using Kiesel gel TM 60 (70–230 mesh) silica gel (from EM Science). The column was packed in hexane, and hexane was used as the developing solvent. Analysis with GC as described above showed 69% cis-9-tricosene, 11% trans-9-tricosene, and 4% tricosane.

Another sample that had been chromatographed using silica gel as described above was heated to 217° C. in a distillation pot and refluxed up through metal Goodloe TM packing for 6–7 hours followed by GC analysis. The results showed 70.9% cis-isomer, 7.5% trans-isomer, and 4.5% tricosane, determined by GC as described above, indicating little or no isomerization after removal of impurities.

EXAMPLE IV

Purification of cis-9-tricosene Using a KOH/MeOH Wash

A sample of crude tricosene was prepared as set forth in Example I and was treated with 6.5 l of 4M HCl, followed by phase separation. The organic phase was washed with 3 l of saturated sodium bicarbonate solution, followed by 2 volumes of a 1M KOH/MeOH solution (an aqueous KOH/MeOH solution was prepared by mixing one part of methanol and one part of water, with a final KOH concentration of 1M). The aqueous phase was then decanted. The organic solvent was removed by rotor evaporation and the residue distilled at 0.1 mm Hg vacuum. The distilled yield based on pure oleyl alcohol was 92.3%, with the final product containing 75% cis-isomer as determined by GC analysis.

That which is claimed is:

1. A process for the purification of a cis-olefin formed by alkylating a sulfonate ester, wherein said cis-olefin is purified from a reaction mixture formed by the alkylation of said sulfonate ester, which process comprises the steps of:
   (a) mixing said reaction mixture with an acid solution selected from the group consisting of hydrochloric acid, sulfuric acid, phosphoric acid, and acetic acid to form a first purification mixture,
   (b) separating said acid solution from said first purification mixture to form a first purification product,
   (c) mixing said first purification product with a $C_1$-$C_4$ alcohol to form a second purification mixture,
   (d) separating said $C_1$-$C_4$ alcohol from said second purification mixture to form a final purification product, and
   (e) distilling said final purification product to yield said purified cis-olefin.

2. The process of claim 1 wherein the acid solution is hydrochloric acid.

3. The process of claim 1 wherein the $C_1$-$C_4$ alcohol is methanol.

4. The process of claim 1 wherein the $C_1$-$C_4$ alcohol is isopropanol.

5. The process of claim 1 wherein the cis-olefin is Z-9-tricosene.

6. A process for the purification of a cis-olefin formed by alkylating a sulfonate ester, wherein said cis-olefin is purified from a reaction mixture formed by the alkylation of said sulfonate ester, which process comprises the steps of:
   (a) mixing said reaction mixture with an acid solution selected from the group consisting of hydrochloric acid, sulfuric acid, phosphoric acid, and acetic acid to form a first purification mixture,
   (b) separating said acid solution from said first purification mixture to form a first purification product,
   (c) mixing said first purification product with a $C_1$-$C_4$ alcohol and an base in solution,
   (d) separating from said $C_1$-$C_4$ alcohol and said base in solution to form a final purification product and
   (e) distilling said final purification product to yield said cis-olefin.

7. The process of claim 6 wherein the $C_1$-$C_4$ alcohol and the base in solution are simultaneously added to said first purification product in step (c).

8. The process of claim 6 wherein the $C_1$-$C_4$ alcohol is added to said purification product before the addition of the base in solution in step (c).

9. The process of claim 6 wherein the $C_1$-$C_4$ alcohol is added to said first purification product after the addition of the base in solution in step (c).

10. The process of claim 6 wherein the cis-olefin is formed utilizing a sulfonate ester synthesis consisting essentially of the following steps:
    (a) reacting a cis-olefinic alcohol with a source of alkali metal ion selected from the group consisting of lithium and sodium ions to form a first reaction product,
    (b) then contacting said thus formed first reaction product with a sulfonyl halide compound wherein the sulfonyl halide compound is selected from the group consisting of an alkyl sulfonyl halide and an aryl sulfonyl halide wherein the halide of said sulfonyl halide compound is selected from the group consisting of chloride and bromide to form a second reaction product,
    (c) then contacting said thus formed second reaction product with a cuprous salt and alkylmagnesium compound selected from the group consisting of dialkylmagnesium and alkylmagnesium halide wherein the halide of said alkylmagnesium halide is selected from the group consisting of iodide, bromide, and chloride to form a third reaction product comprising a cis-olefin wherein the steps are carried out in a suitable organic solvent.

11. The process of claim 9 wherein the $C_1$-$C_4$ alcohol and the base in solution are simultaneously added to said first purification product in step (c).

12. The process of claim 9 wherein the acid solution concentration is in the range of from about 1 molar to 6 molar wherein the volume ratio of said acid solution to said reaction mixture is from about 0.01:1 to about 100:2.

13. The process of claim 11 wherein the temperature range at which said acid solution is mixed with said reaction mixture ranges from about 0° C. to about 40° C.

14. The process of claim 9 wherein the volume ratio of $C_1$-$C_4$ alcohol mixed with said first purification product ranges from a volume ratio of about 0.01:1 to about 100:1 $C_1$-$C_4$ alcohol to first purification product.

15. The process of claim 13 wherein said $C_1$-$C_4$ alcohol is mixed with said first purification product at a temperature range from about 0° C. to about 40° C.

16. The process of claim 9 wherein said base in solution is provided at a concentration range from about 0.5 molar to about 4 molar wherein the volume ratio of said aqueous base solution to said purification product is about 0.1:1 to about 10:1.

17. The process of claim 15 wherein the temperature range at which said base in solution is mixed with said purification product ranges from about 0° C. to about 40° C.

18. The process of claim 9 wherein the cis-olefin is cis-9-tricosene.

19. A process for the purification of a cis-olefin formed by alkylating a sulfonate ester, wherein said cis-olefin is purified from a reaction mixture formed by the alkylation of said sulfonate ester which process comprises the steps of:
    (a) passing said reaction mixture through a suitable silica chromatographic gel packed in an organic solvent to fractionate said reaction mixture, and
    (b) recovering the fraction containing said cis-olefin.

20. The process of claim 18 wherein the cis-olefin is formed utilizing a sulfonate ester synthesis consisting essentially of the following steps:
(a) reacting a cis-olefinic alcohol with a source of alkali metal ion selected from the group consisting of lithium and sodium ions to form a first reaction product,
(b) then contacting said thus formed first reaction product with a sulfonyl halide compound, wherein the sulfonyl halide compound is selected from the group consisting of an alkylsulfonyl halide and an arylsulfonyl halide wherein the halide of said sulfonyl halide compound is selected from the group consisting of chloride and bromide to form a second reaction product,
(c) then contacting said thus formed second reaction product with a cuprous salt and alkylmagnesium compound selected from the group consisting of dialkylmagnesium and alkylmagnesium halide wherein the halide of said alkylmagnesium halide is selected from the group consisting of iodide, bromide, and chloride to form a third reaction product comprising a cis-olefin wherein the steps are carried out in a suitable organic solvent.

21. The process of claim 19 wherein the silica chromatographic gel is a 70–230 mesh silica gel.

22. The process of claim 20 wherein the organic solvent is selected from the group consisting of hexane, pentane, and petroleum ethers.

* * * * *